(12) United States Patent
Phillips

(10) Patent No.: US 10,527,586 B2
(45) Date of Patent: Jan. 7, 2020

(54) METHOD AND SYSTEM FOR JOINT INSPECTION

(71) Applicant: HS Marston Aerospace Limited, Wolverhampton, Staffordshire (GB)

(72) Inventor: Paul Phillips, Bromsgrove (GB)

(73) Assignee: HS MARSTON AEROSPACE LIMITED, Wolverhampton, Staffordshire (GB)

( * ) Notice: Subject to any disclaimer, the term of this patent is extended or adjusted under 35 U.S.C. 154(b) by 153 days.

(21) Appl. No.: 15/657,360

(22) Filed: Jul. 24, 2017

(65) Prior Publication Data

US 2018/0024098 A1    Jan. 25, 2018

(30) Foreign Application Priority Data

Jul. 25, 2016    (GB) .................................. 1612826.6

(51) Int. Cl.
| | |
|---|---|
| *G01N 29/24* | (2006.01) |
| *G01N 29/26* | (2006.01) |
| *G01N 29/44* | (2006.01) |
| *G01N 29/22* | (2006.01) |
| *G01N 29/265* | (2006.01) |
| *G01N 29/46* | (2006.01) |
| *G01N 29/12* | (2006.01) |

(52) U.S. Cl.
CPC ........... *G01N 29/12* (2013.01); *G01N 29/225* (2013.01); *G01N 29/2412* (2013.01); *G01N 29/26* (2013.01); *G01N 29/265* (2013.01); *G01N 29/4427* (2013.01); *G01N 29/46* (2013.01); *G01N 2291/267* (2013.01)

(58) Field of Classification Search
CPC .... G01N 29/12; G01N 29/2412; G01N 29/26; G01N 29/46; G01N 29/225; G01N 29/265; G01N 29/4427; G01N 2291/267
USPC .......................................................... 73/588
See application file for complete search history.

(56) References Cited

U.S. PATENT DOCUMENTS

| | | | | |
|---|---|---|---|---|
| 4,783,988 | A | * 11/1988 | Bao ..................... | G01M 3/2884 73/46 |
| 5,439,157 | A | 8/1995 | Geier et al. | |
| 5,474,225 | A | 12/1995 | Geier et al. | |
| 5,866,820 | A | * 2/1999 | Camplin ............ | G01N 29/0609 73/159 |
| 6,125,703 | A | 10/2000 | MacLauchlan et al. | |
| 6,158,285 | A | 12/2000 | Latimer et al. | |

(Continued)

FOREIGN PATENT DOCUMENTS

DE    2945026 A1    5/1981

OTHER PUBLICATIONS

Welding GAP Control using infrared sensing, Bryan A, Cin et al. Jul. 20, 2001 (Year: 2001).*

(Continued)

*Primary Examiner* — Jacques M Saint Surin
(74) *Attorney, Agent, or Firm* — Cantor Colburn LLP

(57) ABSTRACT

A method of inspecting a joint of a heat exchanger comprises: scanning the heat exchanger 10 with an electromagnetic acoustic transducer (EMAT) sensor 110 by scanning the EMAT sensor 110 over an area of the heat exchanger 10 in a scanning pattern; collecting data from the EMAT sensor 110; analysing the data; and determining a status of the joint based on the analysed data.

16 Claims, 5 Drawing Sheets

(56) References Cited

U.S. PATENT DOCUMENTS

| | | | | |
|---|---|---|---|---|
| 6,282,964 B1* | 9/2001 | Hancock | ............... | G01M 3/24 |
| | | | | 73/622 |
| 6,502,463 B1* | 1/2003 | Clark | ............... | G01L 1/12 |
| | | | | 73/597 |
| 9,217,731 B2* | 12/2015 | Yamamoto | ............... | B23K 31/125 |
| 2008/0178679 A1* | 7/2008 | Hirao | ............... | G01N 29/2412 |
| | | | | 73/643 |
| 2011/0296922 A1* | 12/2011 | Ali | ............... | G01N 29/11 |
| | | | | 73/588 |
| 2015/0204821 A1* | 7/2015 | Adams | ............... | G01N 29/2412 |
| | | | | 73/622 |

OTHER PUBLICATIONS

GB Search Report for Application No. GB1612826.6 dated Nov. 17, 2016. 4 pages.

* cited by examiner

METHOD AND SYSTEM FOR JOINT INSPECTION

FOREIGN PRIORITY

This application claims priority to United Kingdom Patent Application No. 1612826.6 filed Jul. 25, 2016, the entire contents of which is incorporated herein by reference.

TECHNICAL FIELD

The invention relates to a method and system for inspection of a joint in a heat exchanger, particularly to an automated method and system for inspecting a joint in a heat exchanger.

BACKGROUND

Heat exchangers are often used in high performance environments and are subsequently required to perform within very high tolerances. Such high performance heat exchangers may need to be compact, and hence may comprise precision made fluid channels for flow of cooling fluid. However, defects within the heat exchanger or cooling channel may be formed during manufacture, particularly during joining on the constituent pieces of the heat exchanger. Such defects can result in a loss of system integrity, a loss of efficiency, or total system failure, for example by leakage of cooling fluid during service. Therefore, the quality of joints within such heat exchangers is of paramount importance.

Fluid-cooled cold plates are an example of high-performance heat exchangers, and are designed for use in very high power applications where space is at a premium. Manufacture of cold plates typically combines two techniques: machining and vacuum brazing. Firstly, a fluid flow channel defining at least a part of a cooling circuit through the cold plate is machined into at least one plate. Then the machined plate is vacuum brazed to another plate. The machined fluid flow channel may be designed specifically for the chosen application of the cold plate, and may be optimised according to the power and configuration of components to be cooled by the cool plate. Therefore, the positioning of the brazed joints within the cold plate may be determined on a case by case basis and can vary from a simple channel to a complicated circuit (e.g. for high power requirements).

Quality inspection of joints within cold plates, such as brazed joints on internal surfaces, is notoriously difficult and since the joints are internal to the cold plate, straightforward (e.g. visual) inspection of them may be impossible. Moreover, determining the precise location of the joints within the cold plate can be problematic. Conventional methods of inspection include the use of ultrasonic sensors. However, such sensors can be unreliable for various reasons, including a lack of depth penetration through the plate, as well as because of data resolution issues. Further, a coupling fluid needs to be applied to the cold plate to transmit the ultrasonic vibrations from the sensor to the cold plate and back, and hence the cold plate often requires additional cleaning after quality control inspection, thereby increasing the costs of quality control. Because of the various constraints of conventional ultrasound inspection, it is often a manual process carried out by hand. This can make the process slow and susceptible to human error.

Therefore a reliable, efficient, dynamic, and robust inspection method for inspection of joint integrity of heat exchangers is required to help ensure the quality of the heat exchanger after manufacture.

SUMMARY

According to a first aspect of the invention there is provided a method of inspecting a joint of a heat exchanger, the method comprising: scanning the heat exchanger with an electromagnetic acoustic transducer (EMAT) sensor by scanning the EMAT sensor over an area of the heat exchanger in a scanning pattern; collecting data from the EMAT sensor; analysing the data; and determining a status of the joint based on the analysed data.

Electromagnetic acoustic transducers (EMAT) employ electromagnetic (EM) phenomena to induce ultrasonic vibrations in nearby materials. The sensors then measure the interactions of the vibrations and the material using EM phenomena to determine properties of the material. EMAT sensors therefore provide a means of non-destructive testing (NDT) which is non-contact and does not require couplant.

EMAT sensors are known for scanning one-dimensional welds, for example as described in U.S. Pat. No. 6,158,285. The first aspect above proposes a more complex approach, scanning over an area of the heat exchanger. That is, the sensor may be arranged to conduct a scan of at least a portion of a surface of the heat-exchanger by relative movement in two-dimensions of the sensor relative to the heat exchanger. The sensor may therefore be configured to generate a two-dimensional scan of at least part of the heat exchanger. The EMAT sensor may be configured to obtain data by scanning substantially all of the total area of the heat exchanger, or may be configured to obtain data by scanning only predetermined areas of the total area of the heat exchanger. The method may comprise scanning over a surface or (a plurality of surfaces) of the heat exchanger by moving the EMAT sensor in three-dimensions and/or by generating a three-dimensional scan of the heat exchanger.

The joint may be a metal-metal joint, including a brazed, welded or soldered joint. The joint may have a two dimensional shape, for example a joint between surfaces of two parts with heat exchanger features formed by the assembly of the two parts. In one example the joint is a brazed joint with a two dimensional shape, such as a joint between two generally flat plates. It is known to manufacture heat exchangers by joining two parts to form heat exchanger features such as one or more fluid channel between the two parts and brazing is a known technique for this as set out above. The proposed method provides advantages when used with such heat exchangers by allowing for effective inspection of the joins in a non-destructive testing process.

The heat exchanger may be a cold plate, and may be designed for high-performance within small tolerances. In a particular example the heat exchanger is a cold plate and the joint is a brazed joint.

The heat exchanger may comprise a fluid channel for flow of heating or cooling fluid therethrough. The fluid channel may take any form suitable for the purposes for which the heat exchanger is to be used. The positioning of the joint within the heat exchanger may be dependent on the geometry of the fluid channel. The joint may be a joint along heat exchanger features that enclose the fluid channel and/or define the edges of the fluid channel. Thus, the joint to be inspected may only be present in areas of the heat exchanger about the perimeter of the fluid channel. The scanning pattern may include only these areas.

Scanning the EMAT sensor over the heat exchanger may comprise moving the EMAT sensor while holding the heat exchanger stationary, or moving the heat exchanger while holding the EMAT sensor stationary. It may include moving both the EMAT sensor and the heat exchanger simultaneously.

Scanning the heat exchanger with an EMAT sensor may comprise inducing ultrasonic vibrations in the heat exchanger using the EMAT sensor, and registering and measuring the interactions of ultrasonic vibrations within the heat exchanger with an electromagnetic (EM) field generated by the EMAT sensor. That is, reflections from the ultrasonic wave are received by the EMAT device and produce a characteristic electrical signal, which may then be processed. The EMAT may therefore gather frequency information related to both temporal and spatial frequency of the signal from the heat exchanger.

The method may comprise determining the scanning pattern of the EMAT sensor based on a computer model of the heat exchanger. The scanning pattern may include an area (or areas) of the heat exchanger that include the joint, and/or may omit areas of the heat exchanger without the joint. The scanning pattern may be determined by a controller which is configured to control the EMAT sensor. The controller may receive a design used for manufacturing the heat exchanger, and determine the pattern based on that design. For example, a computer-aided design (CAD) model may be processed by the controller to determine the likely location of the joint within the heat exchanger. The controller may then determine a pattern based on that information through which the EMAT sensor is to be moved. For example, the pattern may be in two (spatial) dimensions as described above.

The controller may determine the pattern to minimize the total distance moved by the EMAT sensor (or heat exchanger as appropriate). For example, if the controller determines from the design that there are five locations within the heat exchanger to be scanned, it may employ an algorithm to calculate the shortest path between all five locations, and thereby help minimise the time spent conducting the method. The EMAT may therefore move through the scanning pattern to scan the determined locations of the joint(s). At each determined location, the EMAT sensor may be moved so as to scan an area about that location, to help ensure that the joint is scanned even if it is not in the precise location determined by the controller. Thus, in the example of a joint that is present in areas of the heat exchanger about the perimeter of the fluid channel then the method may include using a scanning pattern that passes over locations where this perimeter is present, and optionally does not include areas where the perimeter is not present, for example areas where there is no joint since there is a void that forms the fluid channel.

The scanning pattern may alternatively cover substantially the whole of the heat exchanger, since the method disclosed herein dynamically allows the location of the joint(s) to be determined and their status assessed. In this way the method may be used to inspect heat exchangers where the internal geometry is not standard and/or is not known accurately.

The step of collecting data may comprise collecting data from a plurality of locations within the scanning pattern, or may comprise collecting data throughout the whole pattern. The collection of data may comprise recording the time or relative time of collection of the EMAT data. The time component of the data may be used to determine the location of the EMAT sensor relative to the heat exchanger for any given signal. Since the scanning pattern is known then the time of collection of the data is related to the location of the sensor within the scanning pattern. Therefore, the information about the heat exchanger obtained by the EMAT sensor at any given point in the pattern can be matched to the location of the EMAT sensor at that time and signals from the EMAT sensor may be matched with locations within the heat exchanger. The collection of data may also or alternatively comprise collecting co-ordinates for the EMAT sensor for its position relative to the heat exchanger.

The step of analysing the data may comprise performing a wavelet transform on the data. Wavelet transforms are a type of time-frequency transformation, and may therefore be used to determine properties of the heat exchanger based on the signals generated and received the EMAT sensor. For example, ultrasonic waves generated in the heat exchanger by the EMAT sensor will propagate within the heat exchanger and will interact with changes in structure therein. An ultrasonic wave which encounters a defect within the heat exchanger will react (e.g. scatter) in a particular way which may be characteristic of the type of defect—a crack in a joint may produce a different signal to a misalignment etc.

Analysis of the signals therefore provides information relating to the structure of the heat exchanger. Wavelet transforms provide both time and frequency information and therefore allow matching of a part of the signal to a location within the heat exchanger, as described above. However, other analytical techniques and transforms may be used, for example, Fourier transforms, short-time Fourier transforms, discrete wavelet transforms, wavelet packet transforms, or Newland transforms etc. Discrete wavelet transforms are particularly useful because they capture information both about the frequency components of the data, but also about the temporal information (i.e. the location in time).

The step of determining a status of the joint may comprise determining a quality of the joint within the heat exchanger. The signals received by the EMAT sensor depend on the structure of the joint and/or the presence of defects in the joint, and therefore a particular type of defect may exhibit a characteristic response to the EMAT sensor. For example, the analysed data may indicate a space or discontinuity (e.g. a crack) within the joint and hence indicate a defect within the heat exchanger. The analysed data may indicate a defect caused by misalignment in the joint. The analysis may include a comparison of the characteristics of the data collected from the EMAT sensor with expected characteristics, for example expected characteristics based on a model or on previously obtained data. Therefore, the status of the joint may be determined as defective. Alternatively, if the signal and/or analysed data do not show a discrepancy, the status of the joint may not be determined to be defective.

Thus, wavelet transforms may be used to extract signal based features that relate to the joint of the heat exchanger. An appropriate wavelet may be used to extract high and low frequency wavelet coefficients, that may in turn be data fused together using a set of predefined rules to form information rich features. These features may then be compared to baseline signals that relate to known good quality joins. If a discrepancy is detected, this may indicate that there is a poor quality joint. The error between measured and expected signals may be used to estimate the severity of the problem.

The step of analysing the data may also comprise, in addition to wavelet analysis or as an alternative thereto, comparison of the data with a database of known defects. The database may comprise exemplary signals corresponding to the known defects, such that a transform of the data does not need to be carried out, and instead the signal may be compared to the database to determine if the signal in question matches a known defect. If the signal corresponds to a known defect, the joint may be classified as defective. If the signal does not correspond to a known defect in the database then a wavelet transform may be carried out to determine a status of the joint.

The method may further comprise updating the database based on the analysed data and/or the determined status of the joint. In this way, the accuracy and extent of the database may be continually improved by each detected defect.

The method described above in relation to the first aspect may therefore be fully automated, dynamic and robust. The automated process may also allow the exact location of the inspected joint and/or problems with the joint to be pinpointed.

The joint referenced herein may refer to any portion of the heat exchanger where two pieces of the heat exchanger are joined together during manufacture. It may be a single point joint, or may be an extended area or geometry.

According to a second aspect of the disclosure there is provided a system for inspecting a joint of a heat exchanger, the system comprising: an EMAT sensor configured to scan over an area of the heat exchanger in a scanning pattern; a controller for controlling the system and configured to: collect data from the EMAT sensor; analyse the data; and determine a status of the joint based on the analysed data.

The EMAT sensor may be mounted to an actuator such as a gantry that is configured to enable scanning of the EMAT sensor over an area of the heat exchanger. For example, the heat exchanger may be scanned in an x-y co-ordinate system, or a scanning pattern as described above in relation to the first aspect.

The controller may be configured to carry out any or all of the method steps described above in relation to the first aspect of the invention.

BRIEF DESCRIPTION OF THE DRAWINGS

Certain exemplary embodiments of the invention will now be described by way of example only and with reference to the accompanying drawings in which.

DETAILED DESCRIPTION

Figure 1:
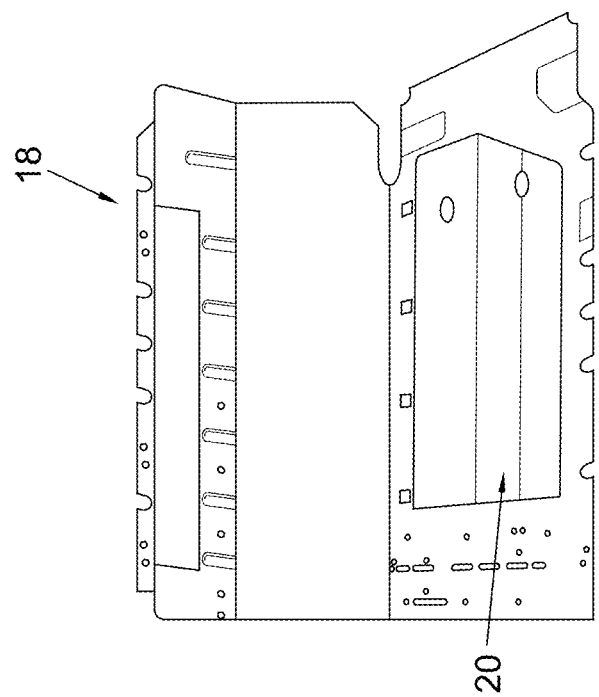
FIG. 1 shows a heat exchanger, particularly a brazed cold plate.
Figure 1:
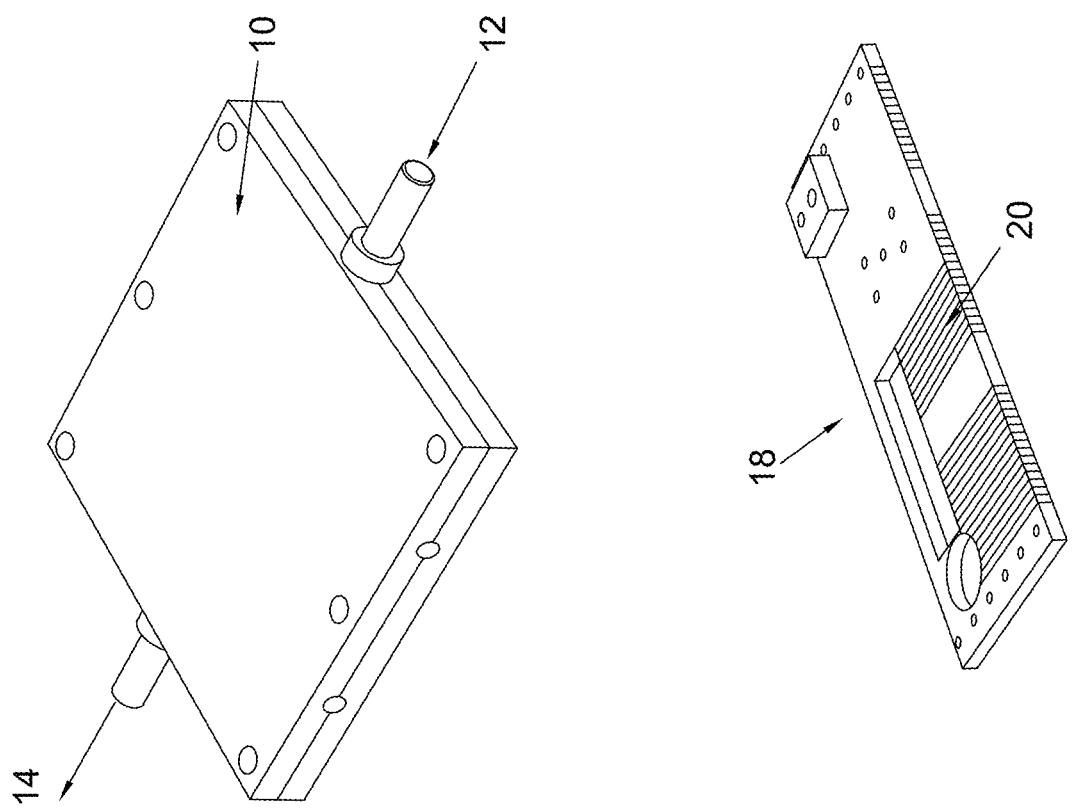

FIG. 1 shows an example of a heat exchanger, particularly a cold plate 10. During use, cooling fluid flows into an inlet at the arrow 12, through cooling channels 16 of the cold plate 10, and out of an outlet in the direction of arrow 14. Also depicted in FIG. 1 are plate-like components 18 of the cold plate. These components are brazed together to form the cold plate 10.

Channels 20 are visible in the components 18. These channels 20 form part of the cooling channels 16 of the finished cold plate 10. The channels 20 may be formed in the components 18, for example, by machining or chemical etching, and arranged such that when the plate-like components 18 are brazed together, the channels 20 cooperate to define the cooling channels 16 of the cold plate through which cooling fluid flows during service.

Figure 2:
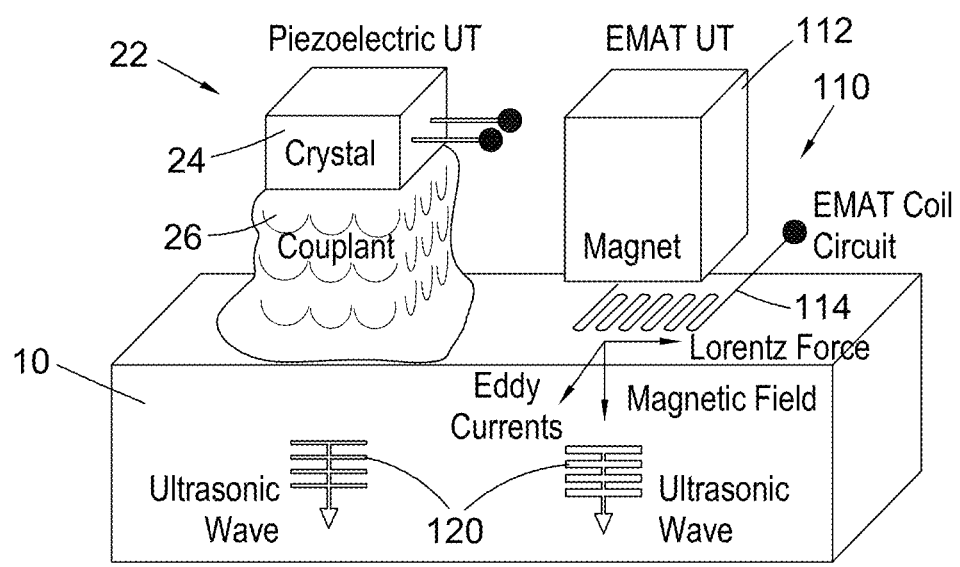
FIG. 2 shows a comparison of ultrasonic wave generation in a material between a piezoelectric transducer and an EMAT.

FIG. 2 shows a schematic example of a piezoelectric ultrasonic transducer (PUT) 22 used for generating ultrasonic waves 120 in the cold plate 10. The ultrasonic waves 120 propagate through the cold plate 10 and are scattered and/or reflected according to the internal structure. The PUT 22 comprises a crystal 24 for generating the ultrasonic waves 120 and requires the use of couplant 26 to transmit the ultrasonic waves 120 from the crystal 24 to the cold plate 10.

Also shown in FIG. 2 is an EMAT sensor 110. The sensor comprises a magnet 112 and a coil circuit 114. The EMAT sensor 110 uses interaction of the magnet 112 and coil circuit 114 to generate ultrasonic waves 120 directly in the cold plate 10 using electromagnetic phenomena. The EMAT sensor does not require the use of a couplant 26.

Figure 3:
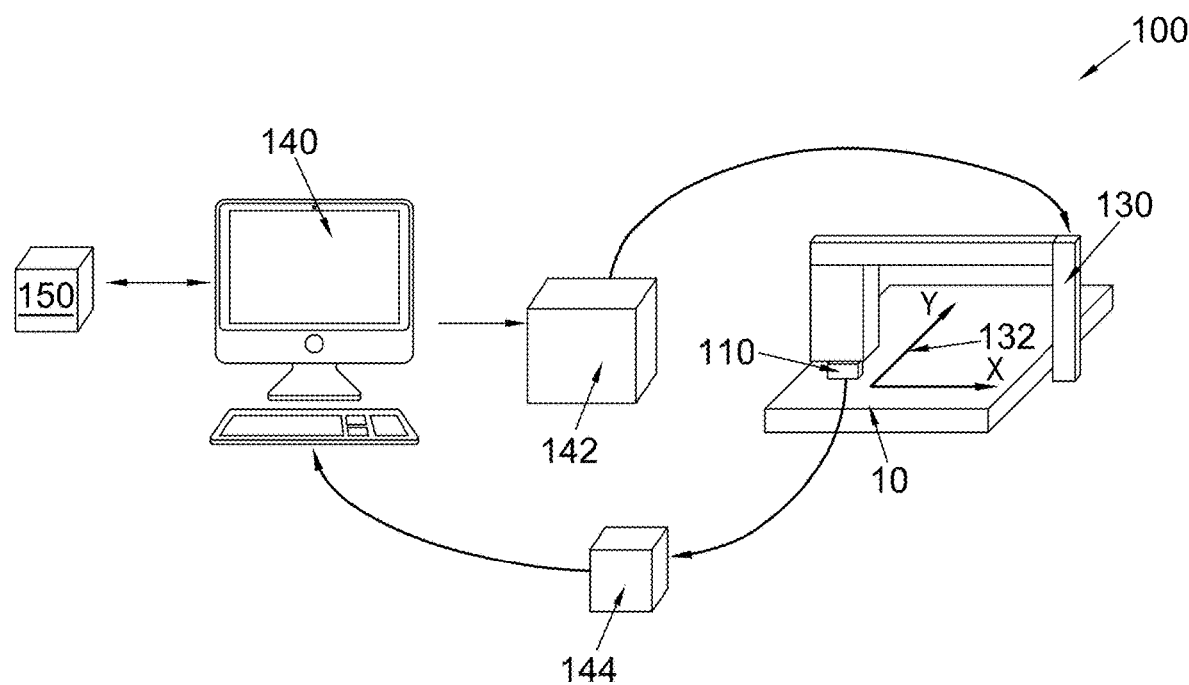
FIG. 3 shows a system for automated inspection of a cold plate.

FIG. 3 shows a system 100 for automated inspection of a cold plate 10. The system 100 includes an EMAT sensor 110 mounted on a gantry 130 and positioned above the cold plate 10. The gantry 130 is controllable to move the EMAT sensor 110 in a plurality of dimensions 132. In the example of FIG. 2, there are two dimensions 132, the X-direction and the Y-direction, and the cold plate 10 in this example is substantially planar. However, the heat exchanger to be inspected may be any desired shape, and the gantry 130 may be configured to scan the EMAT sensor 110 over the surface of the heat exchanger in three dimensions.

A controller 142 is configured to control the gantry 130 and to scan the EMAT sensor 110 over the cold plate 10. A computer 140 is also shown, and although the control 142 is depicted as separate from the computer 140 for reasons of clarity, the controller 142 may be integral to the computer 140. The computer 140 has stored thereon (or receives as needed) information about the cold plate 10 being inspected. This information comprises a design model of the cold plate 10, from which the computer determines a scanning pattern 134 for the controller 142. The scanning pattern 134 may be determined such that it passes over the joint(s) of the brazed cold plate 10 so that the EMAT sensor 110 may inspect them. The computer 140 sends a signal to the controller 142 based upon the determined scanning pattern 134, and the controller 142 in turn controls the gantry 130 to scan the EMAT sensor 110 over the cold plate 10 in the required scanning pattern 134.

Figure 4:
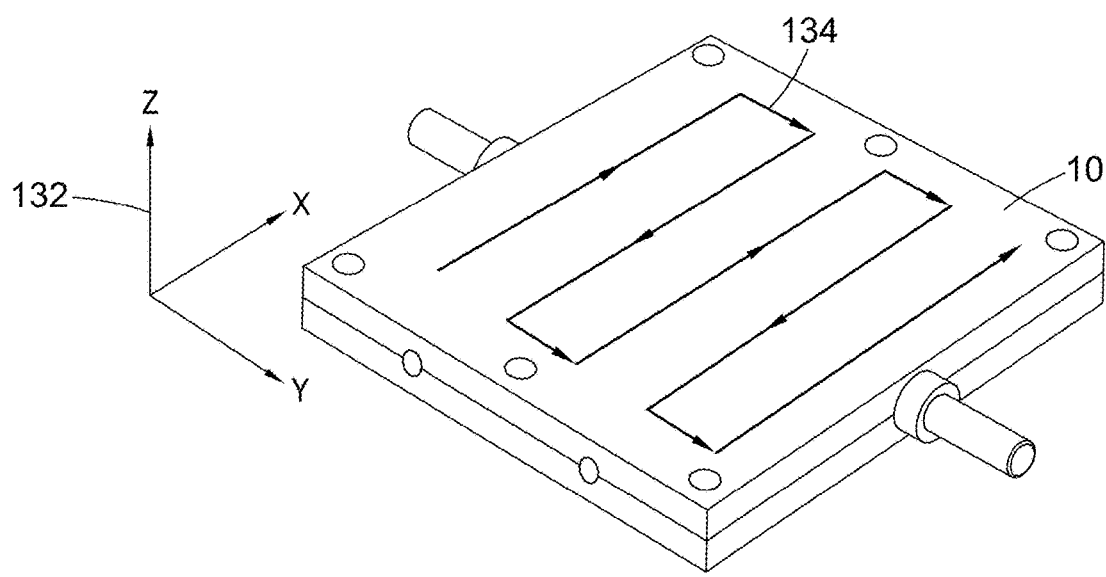
FIG. 4 shows a scanning pattern for inspection of a cold plate.

FIG. 4 shows an example of a scanning pattern 134 of the EMAT sensor 110 as determined by the computer 140. The gantry 130 scans the EMAT sensor 110 over the surface of the cold plate 10 along the scanning pattern 134. In the depicted case, the scanning pattern 134 progresses systematically over substantially the entire surface of the cold plate 10 in two dimensions. However, the pattern may be any form or path as required, and the gantry 130 may move the EMAT sensor 110 in any or all of the dimensions 132 at once (e.g. diagonally in the X- and Y-directions simultaneously).

Returning to FIG. 3, a data acquisition unit 144 may be operatively connected to the EMAT sensor 110 and configured to collect data from the EMAT sensor 110 during the inspection process. The data acquisition unit 144 then sends the collected data to the computer 140 for processing. Although the data acquisition unit 144 is shown as separate from the computer 140, it may be a component thereof.

Although the same computer 140 is shown in FIG. 3 for controlling the EMAT sensor 110 and determining the scanning pattern 134, a different computer or signal processing unit may be used for analysis of the collected data.

The computer 140 is configured to perform analysis of the data to determine the status of the cold plate 10, particularly the quality of the joint(s) therein. The computer 140 is connected to a database 150, which the computer 140 may access during analysis of the data, and/or which the computer 140 may update based on the results of the analysis.

Figure 5:
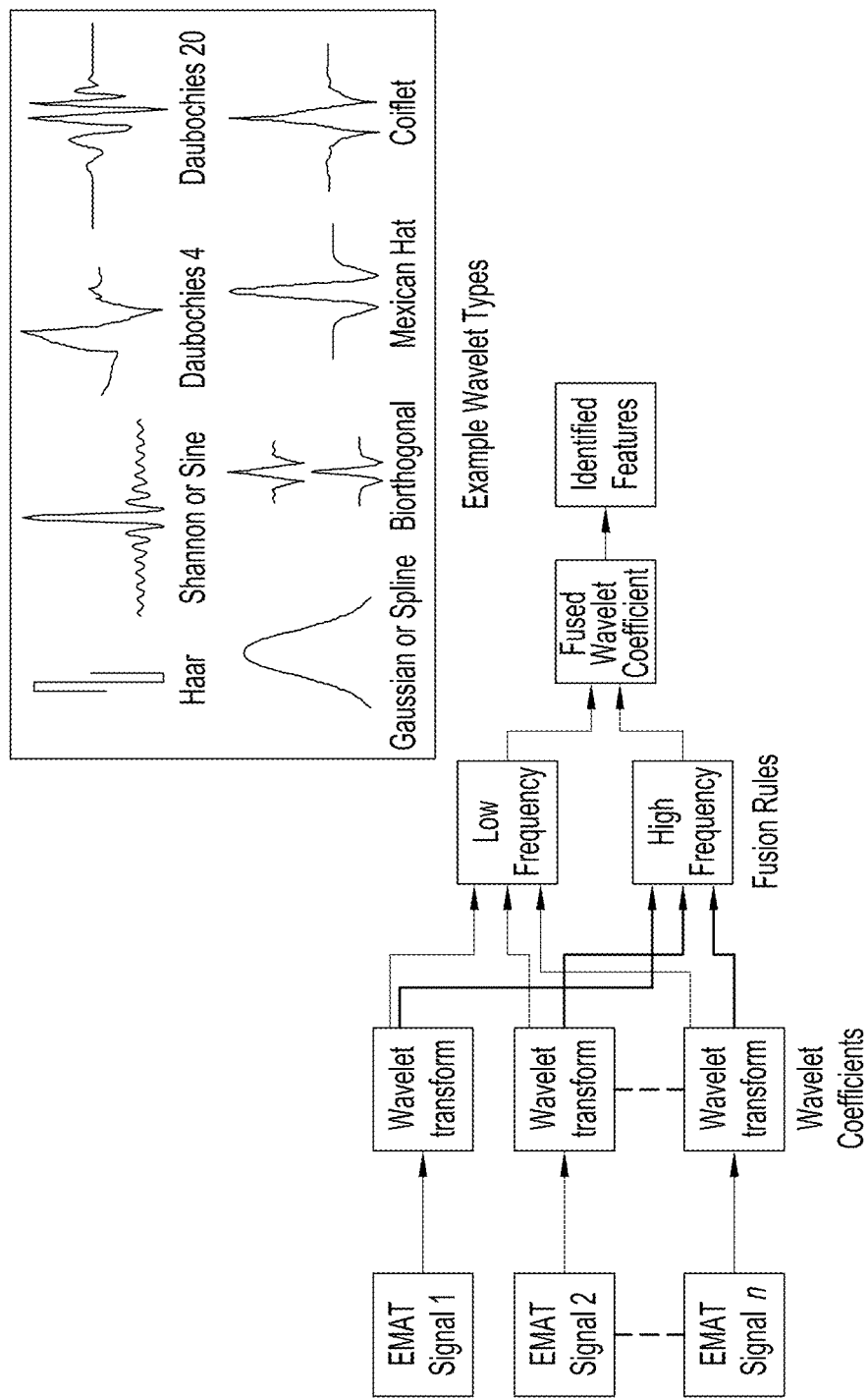
FIG. 5 shows various wavelet types, as well as a schematic diagram of an analysis method for signal processing.

FIG. 5 shows a schematic depiction of the analysis of the collected data performed by the computer 140. The collected data comprises signals from the EMAT sensor 110, which the computer then analyses using a discrete wavelet transform. Discrete wavelet transformations capture both frequency and location (in time) information. The discrete wavelet transform returns high- and low-frequency coefficients, which are indicative of the frequency and temporal behaviour of the signals detected by the EMAT sensor 110, and therefore are also indicative of the properties of the cold plate 10. The high- and low-frequency coefficients can then be employed together to provide information about features of the cold plate 10.

Wavelet transforms may use different wavelets as appropriate. For example, FIG. 5 shows a variety of different wavelet types that might be employed for the transform, including Haar, Daubechies 4 to 20 etc., Sinc, Gaussian, Biorthogonal, Mexican hat, and Coiflet. Different wavelets may be used for different purposes, and any variation or combination may be used for analysis of the collected data, as required.

During the analysis, the computer may or may not compare the data to a baseline model, for example by accessing the database 150 and comparing the measured data with data for known features. Similarities been measured and known data may indicate the occurrence of a known type of defect. The ideal signal may also be known, such that any deviation from an expected signal indicates a defect.

Based on the analysis of the data, different features of the cold plate 10 may be identified. For example, the analysis of the measured signal could provide known frequencies that would be attributed to known defects such as: misaligned braze joints, voids within the joint, un-brazed joints, presence of braze medium run off in the flow channels, and/or cracks in the joint, amongst other things. Such features therefore indicate the status and quality of the joint(s) within the cold plate 10. If a joint does not meet the required standard, the cold plate 10 may be rejected and the likelihood of an in-service failure avoided.

Since the measured data also comprises time information, the resulting features can be traced back to a particular location of the cold plate 10 e.g. by tracing the position of the EMAT sensor 110 and gantry 130 at the relevant time. Therefore, the inspection process can determine not only the quality of a joint within the cold plate, but also its location.

Moreover, once analysis of the data is complete, the database 150 may be updated based upon that analysis. In this way, a library of defects may be compiled and iteratively improved by each inspection, thereby further improving detection and analysis of features during future inspections.

Figure 6:
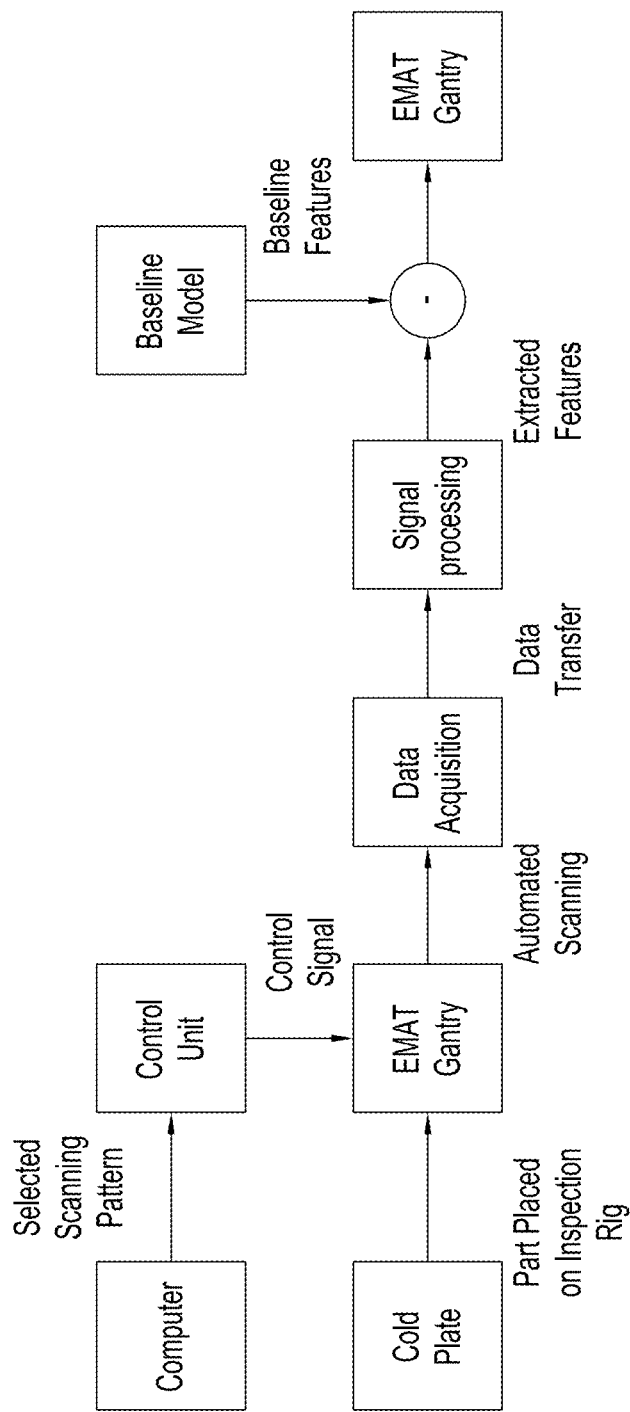
FIG. 6 shows an overview of an inspection method.

FIG. 6 shows an overview of the inspection process. The cold plate 10 is placed to cooperate with the gantry 130 and EMAT sensor 110, while the computer 140 determines the scanning pattern 134 based on a CAD model of the cold plate 10 and instructs the control unit 142 accordingly. The EMAT sensor 110 is scanned over the surface area of the cold plate 10, particularly over the joint(s) therein and the resulting data is collected. The computer then analyses the data using a wavelet transform as described earlier. The analysed data is then compared to a baseline and a decision about the quality of the joint is made.

The methods and systems described herein provide benefits over existing inspections methods, including non-contact inspection with a reliable, low-cost, automated, and fast process, which can be performed by non-skilled workers.

The invention claimed is:

1. A method of inspecting a joint of a heat exchanger, the method comprising:
scanning the heat exchanger with an electromagnetic acoustic transducer (EMAT) sensor by scanning the EMAT sensor over an area of the heat exchanger in a scanning pattern;
collecting data from the EMAT sensor;
analysing the data; and
determining a status of the joint based on the analyzed data;
wherein the scanning pattern is two-dimensional and is based on a computer model of the heat exchanger.

2. The method as claimed in claim 1, wherein the scanning pattern covers an area of the heat exchanger including the joint and omits an area of the heat exchanger without the joint.

3. The method as claimed claim 1, wherein collecting data from the EMAT sensor comprises collecting data from a plurality of locations within the scanning pattern.

4. The method as claimed in claim 1, wherein the collection of data from the EMAT sensor comprises recording the time of collection of the data.

5. The method as claimed claim 1, wherein analysing the data comprises using a wavelet transform.

6. The method as claimed in claim 1, wherein determining a status of the joint comprises determining a quality of the joint within the heat exchanger.

7. The method as claimed in claim 1, wherein analysing data comprises comparing the data to a database of known defects.

8. The method as claimed in claim 7, further comprising updating the database based on the analysed data and the determined status of the joint.

9. The method as claimed in claim 1, comprising inspecting a metal-metal joint, such as a brazed, welded or soldered joint.

10. The method as claimed in claim 1, comprising inspecting a two-dimensional joint.

11. A system for inspecting a joint of a heat exchanger, the system comprising:
an EMAT sensor configured to scan over an area of the heat exchanger in a scanning pattern;
a controller for controlling the system and configured to:
collect data from the EMAT sensor;
analyse the data; and
determine a status of the joint based on the analysed data;
wherein the controller causes the EMAT to scan in a two-dimensional scanning pattern and the scanning pattern is determined based on a computer model of the heat exchanger.

12. The system as claimed in claim 11, further comprising a gantry, wherein the EMAT sensor is mounted to the gantry, the controller controls the gantry, and the gantry is configured to scan the EMAT sensor over the area of the heat exchanger.

13. The system as claimed in claim 11, wherein the scanning pattern covers an area of the heat exchanger including the joint and omits an area of the heat exchanger without the joint.

14. The system as claimed in claim 11, wherein collecting data from the EMAT sensor comprises collecting data from a plurality of locations within the scanning pattern.

15. The system as claimed in claim 11, wherein the collection of data from the EMAT sensor comprises recording the time of collection of the data.

16. The system as claimed in claim 11, wherein analysing the data comprises using a wavelet transform.

* * * * *